United States Patent

Hu et al.

[11] Patent Number: 5,804,366
[45] Date of Patent: Sep. 8, 1998

[54] METHOD AND APPARATUS FOR SODDING MICROVESSEL CELLS ONTO A SYNTHETIC VASCULAR GRAFT

[75] Inventors: Can B. Hu, Irvine; Minh T. Ma, Santa Ana; Than Nguyen, Huntington Beach; Richard Rhee, Diamond Bar; Keith Myers, Lake Forest, all of Calif.

[73] Assignee: Baxter International Inc., Deerfield, Ill.

[21] Appl. No.: 386,048

[22] Filed: Feb. 9, 1995

[51] Int. Cl.$^6$ .................. C12M 3/08; C12N 5/08
[52] U.S. Cl. .................. 435/1.1; 435/240.241; 435/283.1; 435/284.1; 435/297.2; 600/36; 623/1
[58] Field of Search .................. 435/1.1, 283.1, 435/240.241, 240.242, 284.1, 297.2, 297.3, 298.2, 298.1, 308.1; 600/36; 623/1; 210/314, 335; 241/2

[56] References Cited

U.S. PATENT DOCUMENTS

| Re. 19,298 | 8/1934 | Trafton | 210/314 |
|---|---|---|---|
| 3,941,317 | 3/1976 | Kanor | 241/21 |
| 4,350,768 | 9/1982 | Tihon et al. | 435/241 |
| 4,820,626 | 4/1989 | Williams et al. | 623/1 |
| 4,990,131 | 2/1991 | Dardik et al. | |
| 5,035,708 | 7/1991 | Alchas et al. | 623/1 |
| 5,171,261 | 12/1992 | Noishiki et al. | 623/1 |
| 5,356,814 | 10/1994 | Carrico et al. | 435/286 |
| 5,364,790 | 11/1994 | Atwood et al. | 435/288 |
| 5,372,945 | 12/1994 | Alchas et al. | |
| 5,380,589 | 1/1995 | Goodman et al. | |
| 5,390,859 | 2/1995 | Rajasekaran | 241/2 |
| 5,409,833 | 4/1995 | Hu et al. | 435/288 |
| 5,441,539 | 8/1995 | Alchas et al. | 623/66 |

FOREIGN PATENT DOCUMENTS

| 446450 | 12/1990 | European Pat. Off. |
|---|---|---|
| WO 89/03875 | 5/1989 | WIPO |
| WO 94/16099 | 7/1994 | WIPO |
| WO 95/01419 | 1/1995 | WIPO |

*Primary Examiner*—William H. Beisner
*Attorney, Agent, or Firm*—Raymond Sun

[57] ABSTRACT

An apparatus for sodding onto the inner lumenal surface of a synthetic graft of harvested and concentrated microvessel endothelial cells from liposuctioned fat tissues, which harvested cells are formed into a "pellet" of isolated endothelial cells in loose aggregations, includes a sodding tube having a single rigid outer wall bounding a sodding chamber. A filter pack assembly is provided to communicate the pellet of cells from a processing vessel to the graft. This filter pack assembly includes a series of successively finer filter members cooperatively defining a series of turbulent-flow chambers in which aggregations of cells too large to pass through a particular filter are exposed to liquid flow turbulence which is effective to break up the aggregations. A check valve assembly ensures that liquid flow is unidirectional so that sodding of the cells onto the inner lumenal surface of the graft is not interfered with by possible liquid reflux, and sodded cells are similarly not dislodged from the graft by such liquid reflux.

32 Claims, 3 Drawing Sheets

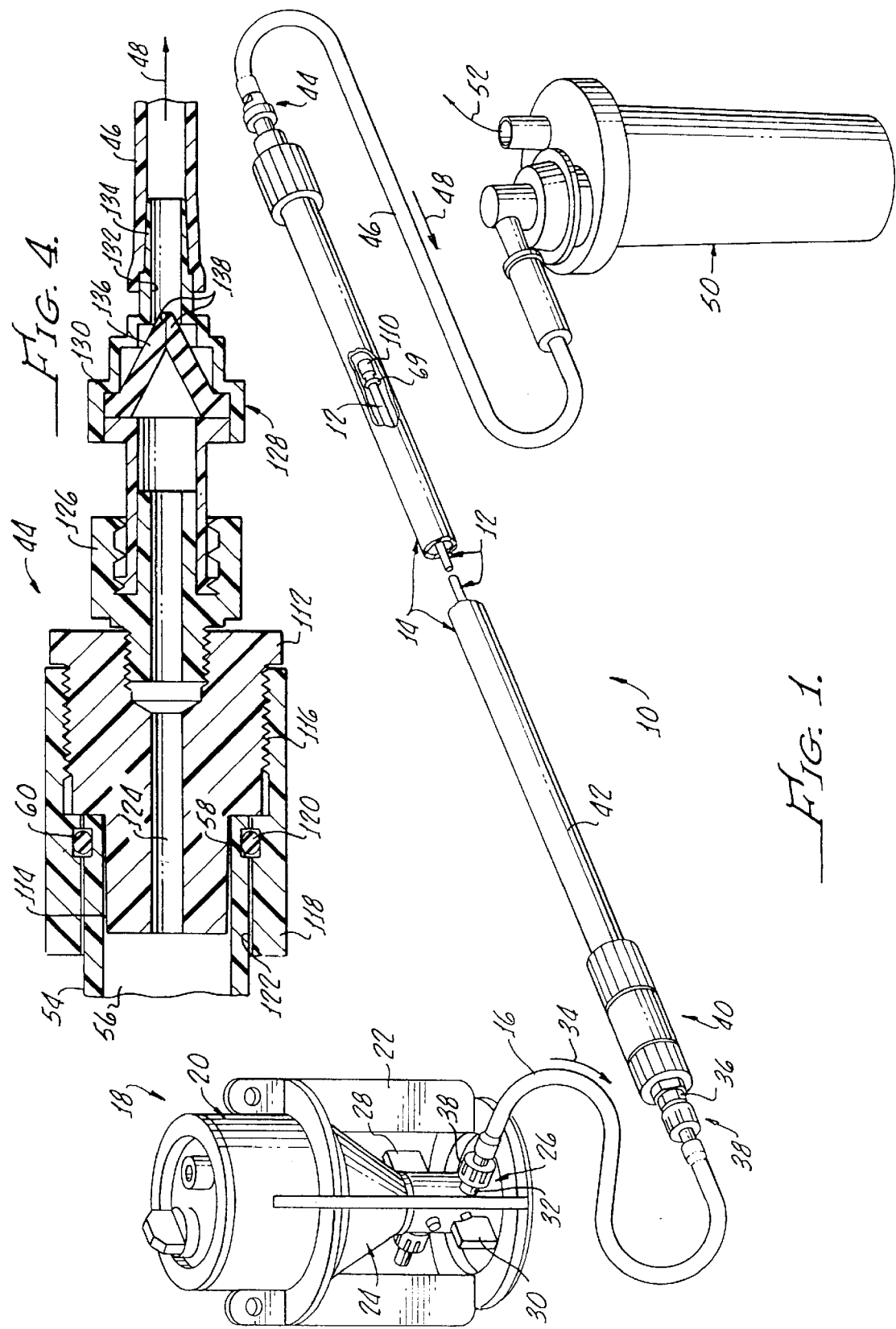

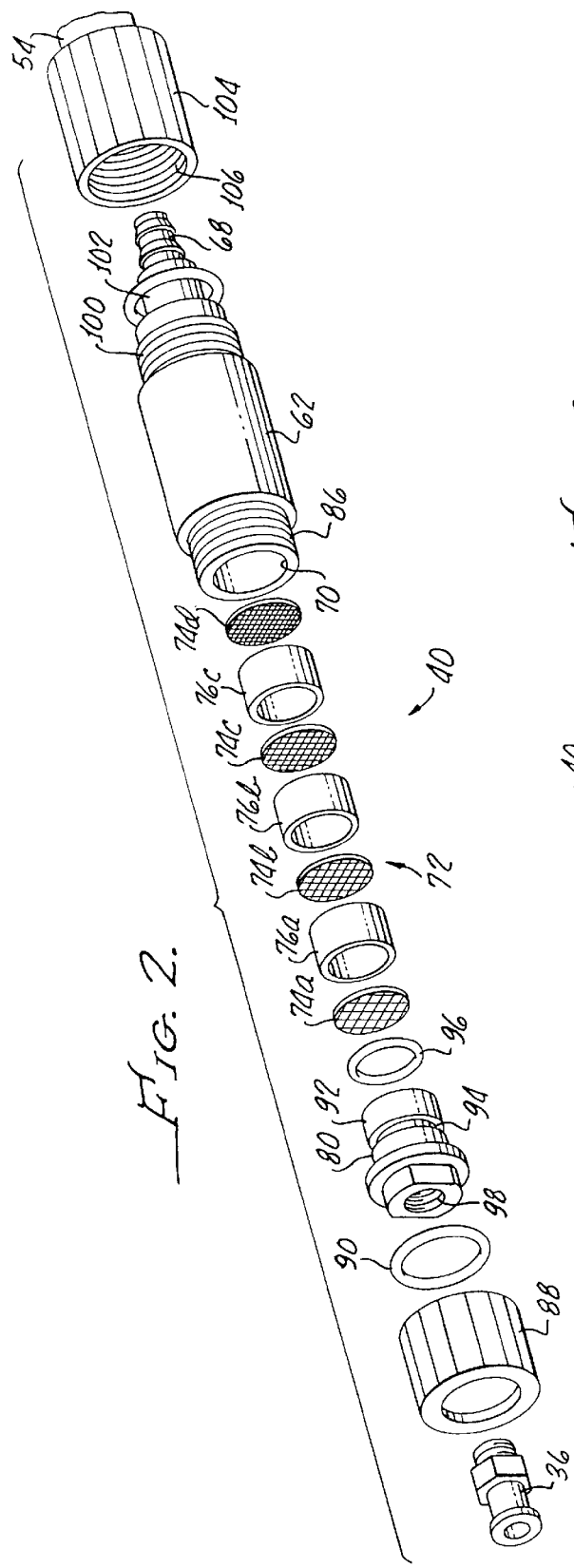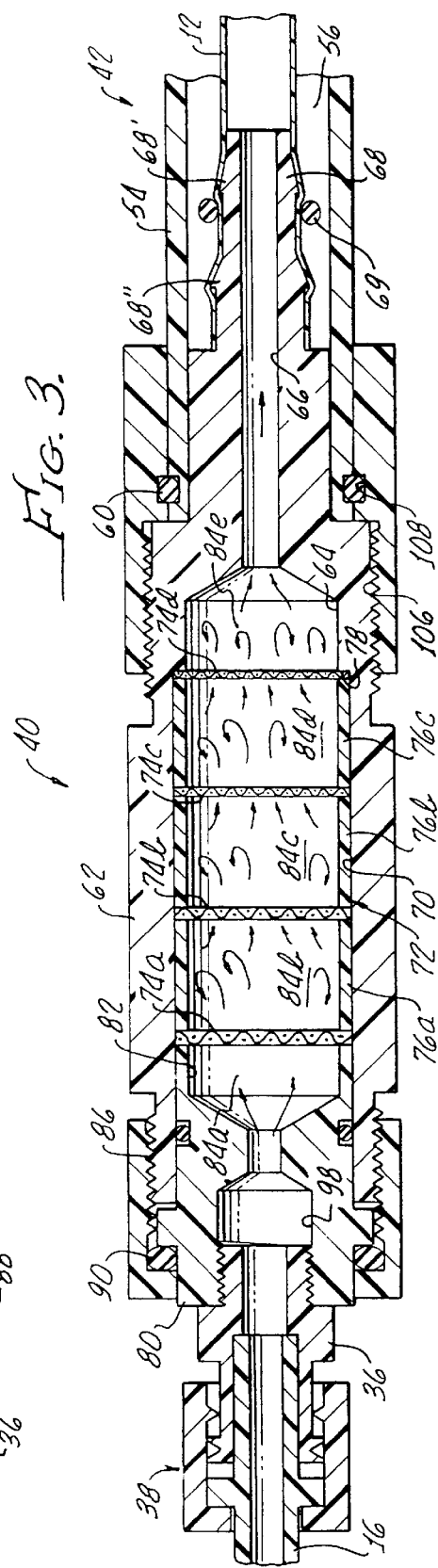

5,804,366

METHOD AND APPARATUS FOR SODDING MICROVESSEL CELLS ONTO A SYNTHETIC VASCULAR GRAFT

CROSS REFERENCE TO RELATED APPLICATION

The present application discloses subject matter which is related to that of U.S. patent applications Ser. No. 08/086,778, filed Jul. 1, 1993, now U.S. Pat. No. 5,409,833; and Ser. No. 08/647,155 filed May 9, 1996, and currently pending; both of which are assigned to the assignee of this application.

BACKGROUND OF THE INVENTION

1. Field of the Invention

The present invention is in the field of vascular grafting. More particularly, the present invention relates to methods and apparatus for isolation of microvessel cells (generally referred to as endothelial cells) from a patient who is to receive a synthetic graft, which graft has a porous inner lumenal surface; and for sodding of the endothelial cells onto this inner lumenal surface of the graft. Deposition of the endothelial cells onto and into the porous inner lumenal surface of the graft is an effective method of reducing or eliminating the formation of post-graft clots (thrombogenicity) on the lumenal surface of the graft. Thus, the occurrence of thrombosis of and emboli in the circulatory system of the patient, which result from blockage of the graft by or sloughing off of such post-graft clots from this inner lumenal surface, is also reduced or eliminated (i.e., thrombogenicity is reduced) by the present invention.

2. Related Technology

A conventional technology for treating a synthetic or naturally occurring surface with microvessel endothelial cells is set forth in U.S. Pat. No. 4,820,626, issued Apr. 11, 1989 to Stuart K. Williams et al. In summary, the teaching of this Williams patent is to obtain tissues rich in microvessel endothelial cells, to separate the endothelial cells from the other tissues, and to place these cells onto the inner lumenal surface of the graft.

The methodology disclosed by the Williams patent is both labor and skill intensive to carry out. Accordingly, the results obtained vary from time to time and are dependent upon the training, skill, and attention of the technician who performs the procedure. Also, the procedure is expensive because of the labor intensive methodology used and the requirement for a highly skilled person to perform the procedure.

Recently, technologies for the harvesting, separation, isolation, culturing, and deposition onto a synthetic vascular graft of microvessel endothelial cells have progressed somewhat beyond the labor and skill intensive laboratory methods initially used. Consequently, the time-consuming methods which were initially used to prove the efficacy of this technology for reducing the thrombogenicity of synthetic vascular grafts are now practiced with apparatus making the procedure less time consuming, less prone to error, more sterile, and safer for the patient and medical personnel.

Further to the above, a conventional apparatus and method for preparing a synthetic vascular graft with a lumenal lining of endothelial cells taken by liposuction from the patient who is to receive the graft is known in accord with U.S. Pat. No. 5,035,708, issued Jul. 30, 1991, to Paul G. Alchas et al. According to the Alchas patent, an endothelial cell isolation device includes a primary chamber tapering downwardly to a secondary chamber or ampule. The secondary chamber also has an upper inlet port and a lower outlet port communicating outwardly of the cell isolation device. Digested fat tissue slurry, with microvessel endothelial cells therein, is introduced into the upper primary chamber, and the isolation device is centrifuged at about 700G for about 7 minutes to produce an endothelial cell product in the form of a "pellet" composed essentially of endothelial cells. This pellet of endothelial cells is then isolated from the fat cells and red blood cells also in the chamber of the isolation device, and is transferred from the cell isolation device to a cell deposition apparatus.

The cell deposition apparatus of the '708 Alchas patent is believed to assert that dispersal of the endothelial cells in a solution of autologous serum and media is effected. From this suspension, the endothelial cells are deposited onto and into the porous inner lumenal surface of a synthetic vascular graft. The cell deposition device includes both an inner and an outer tube. Within the outer tube, a rotator apparatus is arranged to rotate the inner tube along its axis. Rotary fluid fittings are required at each end of the inner tube to allow the microvessel cells in suspension to flow into the rotational inner tube where the graft is located. A heating pad is also located within the outer tube and around the inner tube to effect temperature stabilization of the graft during sodding of the endothelial cells onto the inner lumenal surface of the graft. A vortex/mesh assembly is asserted to break up the endothelial cell pellet and to filter out gross particulates. The endothelial cells are asserted to be re-suspended in autologous serum/media solution and to be drawn onto the inner luminal surface of the graft by vacuum.

However, experience has shown the devices and methods according to the conventional technology are overly complex in their structure and are difficult to use. The results obtained with these conventional devices is not as good as could be hoped for. That is, the pellet of endothelial cells is not as effectively broken up and the cells are not as effectively re-suspended in the solution of serum and/or media in preparation for sodding onto the graft as would be necessary to achieve best utilization of the available cells. Clumps and aggregations of the endothelial cells which are not broken up are trapped before delivery to the graft, or are flushed from the graft with little or no effective sodding of the cells forming these clumps onto the inner lumenal surface of the graft. In fact, a significant deficiency in the apparatus according to the '708 Alchas patent derives from its use of a static mixer as the principle component of the vortex/mesh assembly. Such static mixers are generally used to mix two or more fluid streams which are introduced simultaneously into one end of a single flow path an individual fluid streams. The static mixer is disposed along the length of this single flow path and repeatedly divides and recombines portions of the individual flow streams until a homogeneous single flow of liquid is achieved. These static mixers achieve homogeneity of the fluid stream by repeatedly dividing and re-combining different sub-parts of a fluid stream. When used to mix such viscous fluids as the two parts of an epoxy adhesive, these static mixers do a good job of mixing together the two parts of the epoxy. However, such mixers are not intended to and do not do an effective job of breaking up a pellet or aggregation of solids (such as micro-vessel cells) suspended in a liquid of comparatively low viscosity.

Moreover, with the devices and methods of the conventional technology, the complexity of the structures and methods employed are compounded both by an inefficiency in the separation of the microvessel endothelial cells from the fat cells in the slurry (meaning that a low yield of endothelial cells is provided with which to do the cell deposition onto the inner lumenal surface of the synthetic graft), and with an inefficiency in the utilization of the harvested cells by the cell deposition apparatus. As a result, many microvessel endothelial cells which are present in the fat slurry are simply not recovered or are thrown away with the disposable deposition device without being sodded onto the graft. Consequently, the patient may have to endure a more extensive liposuction than otherwise would be required in order to provide a sufficient number of endothelial cells. While a graft sodded with any level of cells is preferable to an unsodded graft because the former is less thrombogenic, a graft which is more thrombogenic than desired may result with the conventional technology because grafts so sodded may still have an insufficient level of sodding of endothelial cells on their inner lumenal surface.

More particularly, the cell deposition apparatus is believed to be generally ineffective in providing a uniform dispersal of the endothelial cells into the autologous serum and media. Consequently, cells are damaged by the deposition apparatus, or are rendered as a dispersion which includes many comparatively large clumps or aggregations of cells. The damaged cells are not as fully advantageous for deposition on the inner surface of a graft as are healthy, undamaged and viable cells, and the clumps or aggregations of cells will not deposit effectively on the graft surface or will be trapped in the deposition apparatus. That is, such aggregations of cells effectively prevents dispersal of large numbers of the available cells over the surface of the graft, and also will generally be flushed away entirely by flushing of the graft before surgical placement, or by blood flow after surgical placement of the graft.

Yet another conventional apparatus is known in accord with U.S. Pat. No. 5,171,261, issued Dec. 15, 1992 to Y. Noishiki et al. The teaching of the '261 Noishiki patent is believed to be to treat a synthetic vascular graft with tissue fragments or cells, for example, which fragments and cells are entangled into the pores of the porous and fibrous vascular graft. In order to effect this entanglement of the cells and tissue fragments into the pores of the synthetic vascular graft, the graft is placed within a flexible bag, and a perforate tube is placed within the graft. A syringe is connected to the inner tube and a separate tube leads from the space between the graft and outer bag to an external vacuum or pressure source so that fluid pressure can be maintained radially across the graft. With this arrangement the tissue fragments and cells in liquid suspension can be instilled into the pores of the graft. Noishiki does not appear to teach any particular means or method for dealing with the problem of the harvested cells clumping and not depositing effectively on the inner lumenal surface of a graft. Moreover, the apparatus and method disclosed by the '261 Noishiki patent appear to still represent a laboratory-like contrivance of structure and components which will rely heavily upon the skill of a technician for successful practice of the procedure.

However, a need exists to improve and simplify the apparatus and methods used to sod endothelial cells onto the inner lumenal surface of a synthetic vascular graft. That is, a need exists for apparatus and methods which are simple in structure and uncomplicated in their execution, and which provide a favorable consistent result and are not labor or skill intensive. Additionally, a need exists to improve the safety, efficiency in terms of time and skills required and in terms of yield of microvessel cells available for deposition on the graft, manufacturability, and user convenience of the available apparatus for sodding endothelial microvessel cells for use on the vascular graft. In other words, the entire procedure of sodding microvessel endothelial cells in preparation for surgical grafting should be made less of a laboratory-like procedure requiring highly skilled personnel, make-shift apparatus, and considerable time delays; and into a procedure which can be accomplished with little specialized training, in a short time while the graft implantation surgery is underway, and with high sterility and safety for both the patient and the surgical personnel.

SUMMARY OF THE INVENTION

In view of the deficiencies of the related technology as outlined above, a primary object for this invention is to overcome one or more of these deficiencies of the conventional technology.

Another object is to improve the yield or recovery rate of viable microvessel endothelial cells from a pellet of epithelial cells prepared from digested fat slurry preparatory to deposition of these cells on a synthetic vascular graft.

Another object for the present invention is to improve the manufacturability of an endothelial cell sodding apparatus for use in placing microvessel endothelial cells on the inner lumenal surface of a synthetic graft as outlined above.

Still another object for the present invention is to improve the protection afforded to medical personnel with respect to avoiding exposure to blood-borne infectious agents;

Another objective of the present invention is to improve the ease of manufacture for a cell sodding apparatus by considerably simplifying its structure while also improving the performance of this apparatus in comparison to conventional technologies.

Accordingly, the present invention provides a sodding tube assembly particularly adapted for receiving endothelial microvessel cells and other materials, such as a quantity of certain identified and isolated cells from tissues, and for sodding these cells or other materials onto an inner lumenal surface of a tubular synthetic graft having a porous wall, the sodding tube assembly including an elongate semi-rigid and shape-retaining tubular member having a pair of opposite ends; an inlet fitting and filter pack assembly sealingly cooperating with the tubular member at one of the pair of opposite ends, the inlet and filter pack assembly including flow path means for receiving the quantity of cells in liquid and communicating the cells and liquid into the lumen of the graft, and means for defining a plurality of turbulent-flow chambers along the flow path means, the means for defining a plurality of turbulent-flow chambers including a plurality of filter members interposed between adjacent ones of the plurality of turbulent-flow chambers; and an outlet fitting and check valve assembly sealingly cooperating with the tubular member at the other of the pair of opposite ends, the inlet and filter pack assembly and the outlet and check valve assembly cooperating with the tubular member to define a sodding chamber within which the graft is disposed to receive the cells and liquid from the inlet and filter pack assembly into the lumen of the graft and to flow the liquid outwardly through the porous wall of the graft to the sodding chamber, the outlet fitting and check valve assembly defining flow path means leading from the sodding chamber to an outlet from the sodding tube assembly, and including check valve means disposed in the flow path of the outlet fitting and check valve assembly for preventing reflux of liquid along the flow path from the outlet toward said sodding chamber.

Additional objects and advantages of the present invention will be apparent from a reading of the following detailed description of an exemplary preferred embodiment of the invention taken in conjunction with the appended drawing figures in which like reference numerals denote the same features or features which are analogous in structure.

DESCRIPTION OF THE DRAWING FIGURES

FIG. 1 provides a perspective view of an apparatus embodying the present invention in use sodding microvessel cells onto a vascular graft;

FIG. 2 is an exploded perspective view of a fragmentary portion of the apparatus seen in FIG. 1;

FIG. 3 is a greatly enlarged fragmentary cross sectional view of the portion of the apparatus seen in FIG. 2;

Figure 5:
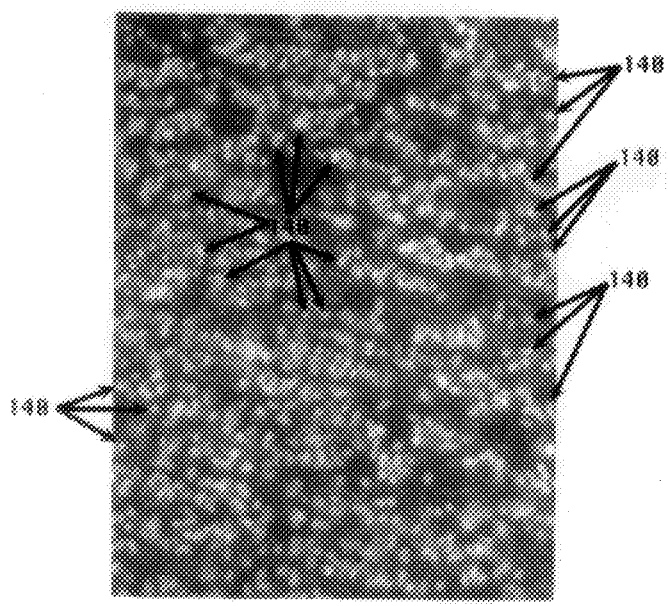
Figure 6:
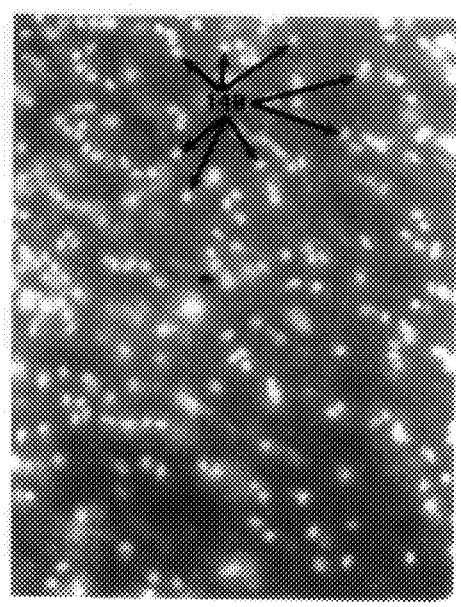
Figure 7:
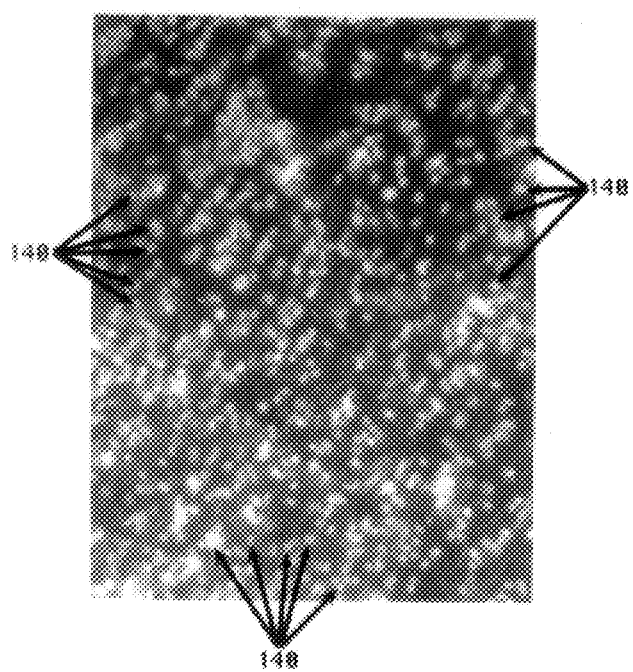

FIG. 4 provides a similarly enlarged fragmentary cross sectional view of another portion of the apparatus seen in FIG. 1; and FIGS. 5–7 provide representations of microphotographs of microvessel cells sodded onto the inner lumenal surface of a graft at three locations along the length of the graft, as is evidenced by photographs of the stained cell nucleus illuminated with ultraviolet light.

DETAILED DESCRIPTION OF THE PREFERRED EXEMPLARY EMBODIMENT

As those ordinarily skilled in the pertinent arts will appreciate, the current technology teaches to harvest tissue which is rich in microvessels, and to separate these microvessel cells from the remainder of the harvested tissue. The separated microvessel endothelial cells are then collected into a "pellet" of such cells by centrifuging a vessel in which the cells have been separated from other collected tissues. The microvessel cells are then used for lining a vascular graft, and the graft is surgically implanted into a patient who donated the tissue. This procedure provides a remarkably reduced thrombogenicity for the synthetic vascular grafts. The donated microvessel endothelial cells are recognized by the body of the patient as "self", so that initial acceptance of the graft into the patient's circulatory system without adverse reactions, as well as the construction of new vascular tissues on the graft are improved.

The present technology teaches to harvest adipose or fat tissues from the patient, usually by use of liposuction, and to digest these fat tissues with an enzyme to free the microvessel cells. The microvessel cells are then separated from the fat cells by straining and centrifuging to form the pellet of these cells. The pellet of cells is then transferred to a cell deposition apparatus, is broken up to individual cells while preventing so far as is possible damage to the cells, and the cells are deposited on the inner lumenal surface of the vascular graft. The complexity of the present technology combined with its inefficient separating of the pellet of cells is outlined above. The present invention provides a much simplified apparatus which is at the same time more effective in achieving separation of the cell pellet into individual cells and sodding of these cells onto the inner lumenal surface of a graft.

Viewing FIG. 1, an apparatus 10 for sodding harvested microvessel cells onto the inner lumenal surface of an elongate tubular synthetic vascular graft 12 is depicted. The graft 12 (only a small portion of which is visible in FIG. 1) is disposed within a similarly elongate tubular sodding tube 14. Further, the apparatus 10 is connected by a flexible conduit 16 to a processing vessel assembly 18. This processing vessel assembly 18 includes a processing vessel 20, and a holder 22 for the processing vessel 20. Closer examination of the processing vessel 20 will show that it includes a chambered upper tissue digestion and separation portion, generally indicated with the numeral 24; and a lower chambered collection structure (referred to as an ampule chamber portion), and generally indicated with the numeral 26. Within this ampule chamber portion 26, microvessel endothelial cells which have been separated from endothelial or adipose cells by enzymatic digestion are concentrated by centrifuging into an elongate vertically extending passage (not seen in the drawing Figures) to form a "pellet" of such cells.

A pair of manually-operable two-way valving members 28 and 30 are carried on the ampule portion 26. The upper one 28 of these two valving members (dependent upon its rotational position) respectively connects the internal passage of the ampule portion 26 at its upper end either to the digestion and separation portion 24 or to a respective luer-type fitting, which fitting is disposed on the back side of the ampule portion 26 as seen in FIG. 1 and is only partially visible in this Figure. In order to provide for flushing of the pellet of endothelial cells from the ampule portion 26, this top luer-type fitting is connected to a source of liquid, such as a solution of serum and/or media (not shown). The lower valve member 30 selectively connects the inner passage of the ampule portion 26 at a location slightly above the lower end of this passage to a luer-type fitting 32. The conduit 16 is connected with the fitting 32 in order to receive the pellet of centrifuged microvessel endothelial cells from the ampule portion 26. Those ordinarily skilled in the pertinent arts will recognize that the positions of the conduit 16 and of the connection to the source of liquid may optionally be reversed.

By a flow of liquid through the ampule portion 26 and into the conduit 16, as is indicated by the arrow 34, the pellet of microvessel endothelial cells is flushed through the conduit 16 and to the sodding tube 14. The sodding tube 14 includes a luer-type fitting 36, to which the conduit 16 is also connected. Viewing FIGS. 1 and 3 in conjunction, it is seen that the conduit 16 at each end includes a male luer-type fitting 38 with a freely-rotational collar portion so that the conduit 16 may be connected with the fittings 32 and 36 without twisting of this conduit or relative rotation of either of the assembly 18 or of tube 14. This feature provides a considerable convenience and ease of handling of the apparatus 10 under operating room conditions.

The sodding tube 14 includes an inlet and filter pack portion, generally indicated with the numeral 40, an elongate sodding chamber tube portion 42, and an outlet fitting and check valve portion 44. Portion 44 provides fluid connection via a conduit 46, and as is indicated by arrow 48, for fluid flow from the graft 12 within tube portion 42 to a liquid catch receptacle 50. Receptacle 50 may be connected to a source of vacuum, as is indicated by arrow 52.

Viewing FIGS. 2 and 3 more particularly, it is seen that the sodding tube chamber portion 42 of sodding tube 14 includes an elongate semi-rigid and shape-retaining tubular member 54, which cooperates with the inlet fitting portion and with outlet fitting portion 44 to define a sodding chamber 56. Graft 12 is extended along the length of chamber 56, as will be more fully explained below. Adjacent to each end, the sodding tube member 54 defines a radially outwardly opening groove, both of which are referenced with the numeral 58. Both ends of the sodding tube member 54 are the same so that this tubular member is reversible and the sodding tube 14 may be assembled without concern for which end of the tube 42 is assembled with the inlet or outlet end fittings. An O-type sealing ring member 60 is received into each groove 58.

The inlet and filter pack fitting portion 40 includes an elongate tubular body 62 defining an axially extending stepped through bore 64. A smaller diameter portion 66 of bore 64 opens axially on a dual-size hose barb 68. Barb 68 outwardly has a first section 68', upon which graft 12 is received, which is sized to sealingly receive such a 4 mm. graft. A second and outwardly larger diameter section 68" of the barb 68 may sealingly receive a 5 mm. graft (not shown). Those ordinarily skilled in the pertinent arts will recognize that the 4 mm. and 5 mm. sizes shown are merely representative, and that the invention may be used to sod grafts of various sizes with cells by providing components of appropriated physical size. An elastic ring 69 is received on the barb 68 and around the proximal end portion of graft 12. This elastic ring 69 is similar to an O-ring, and may be slid along the graft onto the barb 68, subsequently to be rolled along the barb 68 to secure either size of graft on this barb.

A larger diameter portion 70 of the stepped bore 64 receives a filter pack assembly, which is generally referenced with the numeral 72. The filter pack assembly 72 includes four disk-like screen filter members, respectively referenced with the numerals 74a, 74b, 74c, and 74d. These screen filter members 74a–d are successively of finer mesh toward the sodding chamber 56, and are spaced apart from one another by intervening tubular spacer sleeve members 76a, 76b, and 76c. Preferably, the filter member 74a is a square weave of 0.0160 inch stainless steel wire, with a mesh of 20×20 wires, providing openings of substantially 0.0340 inch square, with an open area of 46.2 percent. Preferably, the filter member 74b is a square weave of 0.0085 inch stainless steel wire, with a mesh of 40×40 wires, providing openings of substantially 0.0165 inch square, with an open area of 43.6 percent. Filter member 74c is preferably a square weave of 0.0035 inch stainless steel wire, with a mesh of 88×88 wires, providing openings of substantially 0.0079 inch square, with an open area of 47.9 percent. Finally, filter member 74d is preferably a square weave of 0.0011 inch stainless steel wire, with a mesh of 325×325 wires, providing openings of substantially 0.0020 inch square, with an open area of 41.6 percent. Consequently, it is apparent that cell aggregations larger than the openings of the filter member 74d cannot pass to the graft 12. Understandably, individual cells and smaller aggregations of cells pass through the filters 74a–d, and into the lumen of the graft 12. Importantly, the open area of each filter member 74a–d is similar, and the fluid flow resistance of these filter members is also similar. Consequently, a selected and controlled level of turbulence is achieved both upstream and downstream of each of the filter members 74a–d. Those ordinarily skilled in the pertinent arts will recognize that the stainless steel wire of the screens 74a–d is preferably coated with parylene in order to lower the surface energy of the surface exposed to the viable cells. Alternatively, as a substitute for metallic screens 74, screen or mesh material of appropriate filament size to provide the necessary opening sizes and open areas, and formed of polymer material which has sufficient mechanical strength to sustain the pressure differential across these filter members may be used in the filter pack assembly 72.

The screen filter member 74d rests upon a step 78 on bore 64, while the screen member 74a is engaged by a closure member 80 defining a recess 82 confronting the screen member 74a. Consequently, a series of chambers 84a, 84b, 84c, 84d, and 84e each successively closer to the sodding chamber 56 are defined within the tubular body 62. This tubular body 62 outwardly defines a thread portion 86 upon which a tubular nut member 88 is threadably engageable. This nut member 88 traps an O-ring type sealing member 90, while the closure member 80 includes a cylindrical portion 92 upon which a groove 94 is defined. An O-ring type of sealing member 96 is received into the groove 94, and sealingly cooperates with the inner surface of the tubular body 62. Thus, redundant sealing is provided at the interface of the closure member 80 and tubular body 62 to assure that blood products are not lost into the environment where surgical and laboratory personnel are working with the apparatus 10.

The luer fitting 36 is threadably received at an end of a stepped through bore 98, a larger diameter portion of which defines the recess 82. In order to secure the tubular body 62 sealingly to the sodding chamber tubular member 54, the body 62 outwardly defines a thread portion 100 leading to a cylindrical portion 102. The cylindrical portion 102 is sized to fit closely within the tubular member 54. A nut member 104 is threadably received upon the thread portion 100, and defines a stepped bore 106. The O-ring member 60 is trapped in a portion 108 of the bore 106 when the nut member 104 is threadably engaged with thread portion 100 with the cylindrical portion 102 inserted into the tubular member 54, viewing FIG. 3.

Returning for a moment to a consideration of FIG. 1, is seen that the graft 12 is disposed within and along the length of the tubular member 54. One end of the graft is sealingly secured to the dual-size barb 68. A portion of the tubular member 54 is broken away in FIG. 1 solely for purposes of illustration to reveal that a proximal end of the graft 12 is closed by a barbed and dual-size plug member 110. Similarly to the barb 68, an elastic ring 69 secures the plug member 110 in the distal end portion of graft 12. Thus, it will be appreciated that the liquid introduced into the graft is forced to flow through the porous wall of this graft. However, the graft acts as a filter with respect the microvessel endothelial cells, so that these cells are deposited onto and into the inner lumenal surface of the graft 12.

Attention now to FIG. 4 will show that the outlet and check valve fitting portion 44 includes a tubular body 112. Similarly to the tubular body 62, this body 112, includes a cylindrical portion 114 sized to fit within the tubular body 54, and a thread portion 116. A nut member 118 threadably engages the thread portion 116 and forces the O-ring 60 sealingly into a portion 120 of a stepped bore 122 of this nut member 118. The tubular member 112 defines a through bore 124, an outer portion of which is threaded. A male luer-type fitting 126 is threadably and sealingly received into the bore 124, and provides for a check valve assembly 128 to be connected with the bore 124. This check valve assembly 128 includes a tubular body 130 defining a stepped through bore 132. The bore 132 terminates in a hose barb portion 134 to which the conduit 46 is connected. Within bore 132 is sealingly disposed a resilient polymeric duck-bill type valve body 136. This valve body 136 includes a pair of mutually engaging and cooperating pressure-responsive lips or "duck bill" portions 138 which sealingly cooperate with one another to prevent fluid flow from conduit 46 toward chamber 56, but which will yieldably disengage from one another to allow fluid flow in the opposite direction.

Having considered the structure of the apparatus illustrated in FIGS. 1–4, attention may now be directed to their use and function. As those ordinarily skilled in the pertinent arts will know, adipose or fat tissue, which is rich in microvessel cells, is harvested from a patient who is to receive a synthetic vascular graft. This harvesting may preferably be conducted by use of a liposuction apparatus (not shown). Most preferably, the tissue harvesting may be conducted using an apparatus as disclosed in U.S. patent application Ser. No. 08/647,155, which was identified above, and the disclosure of which is hereby incorporated by reference as though it were fully set out. The harvested fat tissue immediately from the body and while still warm is injected via a port on the top of the process vessel 20 into a chamber defined within the upper portion 24 of the process vessel so that this tissue resides within a screen basket assembly (not shown) held within this vessel. The harvested fat tissue is then rinsed with sterile liquid to remove most of the connective tissue and blood cells which have been collected by the liposuction process.

Next, an enzymatic digesting material, such as collagenase, which is also warmed to body temperature is introduced into the upper chamber of portion 24. The process vessel 20, which is already in its holder 22, is placed into a protective outer canister (not shown), and this canister is closed with a lid (also not shown). This process vessel assembly with the rinsed fat tissues and enzymatic digestion material is placed into a warm air oven upon an agitation plate. The warm air oven serves to preserve the tissues at about body temperature, and to facilitate digestion with the enzymatic material to free the microvessel cells. This digestion and freeing of the microvessel cells is assisted by agitation.

Directly from the warm air oven and agitation, the process vessel assembly 18 is transferred to a centrifuge. Again at this stage of the process, the holder 22 and closed canister (not shown) serve to prevent spilling of the contents of the process vessel 20, and to protect medical personnel from contact with patient tissues and body fluids. Preferably, this process is carried out in accord with the teaching of U.S. patent application Ser. No. 08/086,778, identified above, now U.S. Pat. No. 5,409,833, and the disclosure of which is hereby incorporated by reference as though it were fully set out. The centrifuge is operated at about 700 Gs for a time sufficient to separate the freed microvessel cells from the fat cells in the chamber within upper portion 24. During this centrifuging operation, the valving members 28 and 30 are in the positions necessary to communicate the upper chamber of the process vessel 20 with the ampule chamber within lower portion 26. Consequently, a "pellet" of microvessel cells is formed in the ampule chamber portion 26. A small residue of packed red blood cells and other solid debris may be formed in the very bottom of the ampule chamber portion 26.

After the process vessel assembly 18 is removed from the centrifuge, the vessel 20 in its holder 22 is removed from the canister (not shown), and placed in association with the sodding tube 14 containing the synthetic graft 12 which the patient is to receive. This sodding tube 14 may preferably be supplied as a sterile assembly including the graft 12 already in sodding chamber 56. The sterile sodding tube and graft are removed from their sterile shipping package immediately prior to connection of the conduits 16 and 46 in order to assist in best preserving aseptic conditions for the sodding process.

In order to transfer the pellet of microvessel cells from the ampule chamber portion 26 of the process vessel 20 to the sodding tube 14, a source of sterile buffered liquid at about body temperature is connected to the luer fitting associated with valve member 28. This source of liquid may be elevated somewhat to assist in the necessary liquid flow. The valve member 28 is moved to the position communicating the liquid into the upper end of the ampule chamber portion 26, which simultaneously separates the ampule portion 26 from the processing chamber portion 24. The luer fitting 32 is connected to the sodding tube 14 by conduit 16, and the valve member 30 is manually turned to the position communicating the ampule chamber portion with the fitting 32. Turning the valve member 30 in this way also separates the small quantity of packed red blood cells and other debris which collects in the bottom of the passage of the ampule chamber portion 26 from communication with luer fitting 32. Additionally, the sodding tube 14 is evacuated so that a partial vacuum assists in pulling liquid from the source through the ampule chamber portion 26, through the conduit 16, through the filter pack portion 40, and into the inner lumen of the graft 12. As described above, the liquid is then forced to flow through the porous wall of the graft 12 so that the microvessel endothelial cells are deposited onto and into the porous surface of this graft 12.

Consideration of FIG. 3 once again will reveal (as is indicated by the fluid flow arrows on this figure) that a selected and controlled level of fluid flow and turbulence is maintained in each one of the chambers 84a–e by the filter members 74a–d. This level of fluid flow and turbulence is selected to effectively break up the pellet of microvessel endothelial cells into individual cells and successively smaller aggregations of cells. That is, the pellet of cells initially may be considered as a loose aggregation of cells, which when broken up forms individual cells loose in the liquid medium and a multitude of smaller aggregations of cells of various sizes. The individual cells flow freely downstream into the lumen of the graft 12 in sodding chamber 54. Aggregations of cells which are small enough to pass through the filter 74a may or may not pass through filter 74b, and so on with the following filters 74c and 74d. Aggregations of cells which are not small enough to pass through a particular filter will be exposed to the turbulence and a gentle "buffeting" because of the selected level of fluid flow maintained in the chambers 84a–e. The level of turbulence and fluid flow is balanced so that cells are not excessively damaged by impacts with the filter members, and are not lodged into the interstices of the filter members 74a–d. Consequently, the larger aggregations in each chamber 84a–d are successively broken up into progressively smaller aggregations, freeing individual cells and smaller aggregations with each successive break up of larger aggregations. By this process, a high yield of viable microvessel endothelial cells is provided for sodding onto the inner lumenal surface of the graft 12. The check valve assembly 128 prevents any possible reflux of liquid which could interfere with sodding of cells onto the surface of the graft 12.

Construction and testing of actual apparatus 10 for sodding harvested microvessel cells, and use of this apparatus to sod cells onto the inner lumenal surface of grafts 12 in accord with the present invention has shown a remarkable improvement in the yield of microvessel cells per gram of fat tissue processed. Consequently, the reduction in thrombogenicity of a synthetic graft which can be effected by lining the graft with microvessel cells from the patient can be improved by use of the present invention. Also, the efficacious number of microvessel cells necessary to treat a synthetic graft may be obtained with a smaller extraction of adipose tissue from the patient.

FIGS. 5–7 provide representations of microphotographs of microvessel cells sodded onto the inner lumenal surface of a graft at three locations along the length of the graft, as is evidenced by photographs of the stained cell nucleus (indicated with the representative reference numeral 140) taken while the stained cells were illuminated with ultraviolet light. These depictions of the microphotographs indicate that a more than adequate level of cell sodding is present on the inner lumenal surface of the graft 12. FIG. 5 is a depiction of an area of the graft slightly distally of the barb 68. FIG. 6 is taken at mid-length of the graft 12. FIG. 7 represents a microphotograph taken just proximally of the plug member 110, recalling FIG. 1. These Figures illustrate the uniform distribution of the isolated cells on the inner surface of the graft 12. Thus, it is seen that all or a selected portion of the graft 12 may be surgically implanted with the graft providing a low thrombogenicity because of the sodded cells on the inner lumenal surface of this graft.

While the present invention has been depicted, described, and is defined by reference to a particularly preferred embodiment of the invention, such reference does not imply a limitation on the invention, and no such limitation is to be inferred. The invention is capable of considerable modification, alteration, and equivalents in form and function, as will occur to those ordinarily skilled in the pertinent arts. The depicted and described preferred embodiment of the invention is exemplary only, and is not exhaustive of the scope of the invention. Consequently, the invention is intended to be limited only by the spirit and scope of the appended claims, giving full cognizance to equivalents in all respects.

We claim:

1. A sodding tube assembly for use in receiving a quantity of certain isolated cells from tissues and for sodding the cells onto an inner lumenal surface of a tubular synthetic graft having a porous wall, said sodding tube assembly comprising:

an elongate tubular member having a pair of opposite ends;

an inlet fitting and filter pack assembly sealingly cooperating with said tubular member at one of said pair of opposite ends, said inlet fitting and filter pack assembly defining an inlet flow path for receiving the cells and communicating the cells into the lumen of the graft, and a plurality of filter members cooperatively defining a number of turbulent-flow chambers successively along said inlet flow path; and an outlet fitting and check valve assembly sealingly cooperating with said tubular member at the other of said pair of opposite ends and cooperating with said tubular member and said inlet fitting and filter pack assembly to define a sodding chamber within which said graft is disposed to receive the cells from said inlet fitting and filter pack assembly into the lumen of the graft and to flow a liquid outwardly through said porous wall of the graft to said sodding chamber, said outlet fitting and check valve assembly defining an outlet flow path leading from said sodding chamber to an outlet from said sodding tube assembly, and including a check valve device disposed in said outlet flow path for preventing reflux of liquid along said flow path from said outlet toward said sodding chamber.

2. The sodding tube assembly of claim 1 wherein said inlet fitting and filter pack assembly defines four turbulent-flow chambers each preceding a respective one of said filter members.

3. The sodding tube assembly of claim 2 wherein each of said plurality of filter members defines substantially the same open area.

4. The sodding tube assembly of claim 1 wherein each of said plurality of filter members is of progressively finer opening size along said flow path toward said sodding chamber.

5. The sodding tube assembly of claim 1 wherein at least one of said plurality of filter members is formed of polymer material.

6. The sodding tube assembly of claim 1 wherein said plurality of filter members includes four filter members, a first filter member being formed of a square weave of 0.0160 inch wire, with a mesh of 20×20 wires, providing openings of substantially 0.0340 inch square, with an open area of 46.2 percent; a second filter member positioned downstream of the first filter member and being formed of a square weave of 0.0085 inch wire, with a mesh of 40×40 wires, providing openings of substantially 0.0165 inch square, with an open area of 43.6 percent; a third filter member positioned downstream of the second filter member and being formed of a square weave of 0.0035 inch wire, with a mesh of 88×88 wires, providing openings of substantially 0.0079 inch square, with an open area of 47.9 percent; and a fourth filter member positioned downstream of the third filter member and being formed of a square weave of 0.0011 inch wire, with a mesh of 325×325 wires, providing openings of substantially 0.0020 inch square, with an open area of 41.6 percent.

7. The sodding tube assembly of claim 6 wherein said wires are formed of stainless steel.

8. The sodding tube assembly of claim 1 wherein said plurality of filter members are coated with a material selected to reduce the surface energy of said wires.

9. The sodding tube assembly of claim 8 wherein said plurality of filter members are coated with parylene.

10. The sodding tube assembly of claim 1 wherein said inlet fitting and filter pack assembly includes a tubular body, said tubular body defining a barb member extending therefrom into said elongate tubular member for receiving thereon the synthetic graft, the barb member defining a plurality of barbs, each having a different diameter to accomodate synthetic grafts of different diameters.

11. The sodding tube assembly of claim 1 wherein said inlet fitting and filter pack assembly includes a tubular body defining a stepped through bore; said tubular body including a cylindrical portion receivable into one of said pair of opposite ends of said tubular member; a sealing member disposed in sealing relation with said tubular body and said elongate tubular member, and a nut member engaging said inlet fitting and filter pack assembly and sealingly securing said tubular body thereto.

12. The sodding tube assembly of claim 11 wherein said stepped through bore of said inlet fitting and filter pack assembly further receives a plurality of spacer members interposed individually between adjacent ones of said plurality of filter members.

13. The sodding tube assembly of claim 11 wherein said tubular body further includes a closure member closing an end of said stepped through bore remote from said tubular member, said closure member defining a recess confronting a first of said plurality of filter members and defining a first one of said plurality of turbulent-flow chambers.

14. The sodding tube assembly of claim 1 wherein said check valve of said outlet fitting and check valve assembly includes a check valve member disposed in said outlet flow path, the check valve member comprising a pair of pressure-responsive lips sealingly cooperating to prevent liquid reflux along said outlet flow path from said outlet toward said sodding chamber, said pair of lips disengaging from one another to allow liquid flow from said sodding chamber toward said outlet.

15. The sodding tube assembly of claim 1 further including a conduit for connecting a source of the isolated cells from tissues with said sodding tube assembly, said conduit at each end thereof including a male luer-type connector with a freely rotational fastening collar, and said sodding tube assembly including a female luer-type connector carried upon said inlet fitting and filter pack assembly and communicating with said inlet flow path for receiving the quantity of cells in liquid and communicating the cells and liquid together into the lumen of the graft.

16. A sodding tube assembly for use in receiving a quantity of certain isolated cells from tissues and for sodding the cells onto an inner lumenal surface of a tubular synthetic graft having a porous wall, said sodding tube assembly comprising:

an elongate tubular member defining a sodding chamber for receiving the synthetic graft and having a pair of opposite ends; and an inlet fitting and filter pack assembly sealingly cooperating with said tubular member at one of said pair of opposite ends, said inlet fitting and filter pack assembly defining an inlet flow path for receiving the cells and communicating the cells into the lumen of the graft, and a plurality of filter members cooperatively defining a number of turbulent-flow chambers successively along said inlet flow path, said inlet fitting and filter pack assembly further comprising a tubular body, said tubular body defining a barb member extending therefrom into said elongate tubular member for receiving thereon the synthetic graft, the barb member defining a plurality of barbs, each having a different diameter to accomodate synthetic grafts of different diameters.

17. The sodding tube assembly of claim 16, further comprising an outlet fitting assembly sealingly cooperating with said tubular member at the other of said pair of opposite ends and cooperating with said tubular member and said inlet fitting and filter pack assembly to define the sodding chamber within which said graft is disposed to receive the cells from said inlet fitting and filter pack assembly into the lumen of the graft and to flow a liquid outwardly through said porous wall of the graft to said sodding chamber, said outlet fitting assembly defining an outlet flow path leading from said sodding chamber to an outlet from said sodding tube assembly.

18. The sodding tube assembly of claim 17, wherein said outlet fitting assembly further includes a check valve device disposed in said outlet flow path for preventing reflux of liquid along said flow path from said outlet toward said sodding chamber.

19. The sodding tube assembly of claim 18 wherein said check valve of said outlet fitting assembly includes a check valve member disposed in said outlet flow path, the check valve member comprising a pair of pressure-responsive lips sealingly cooperating to prevent liquid reflux along said outlet flow path from said outlet toward said sodding chamber, said pair of lips disengaging from one another to allow liquid flow from said sodding chamber toward said outlet.

20. The sodding tube assembly of claim 16 wherein said inlet fitting and filter pack assembly defines four turbulent-flow chambers each preceding a respective one of said filter members.

21. The sodding tube assembly of claim 16 wherein each of said plurality of filter members defines substantially the same open area.

22. The sodding tube assembly of claim 16 wherein each of said plurality of filter members is of progressively finer opening size along said flow path toward said sodding chamber.

23. The sodding tube assembly of claim 16 wherein at least one of said plurality of filter members is formed of polymer material.

24. The sodding tube assembly of claim 16 wherein said plurality of filter members includes four filter members, a first filter member being formed of a square weave of 0.0160 inch wire, with a mesh of 20×20 wires, providing openings of substantially 0.0340 inch square, with an open area of 46.2 percent; a second filter member positioned downstream of the first filter member and being formed of a square weave of 0.0085 inch wire, with a mesh of 40×40 wires, providing openings of substantially 0.0165 inch square, with an open area of 43.6 percent; a third filter member positioned downstream of the second filter member and being formed of a square weave of 0.0035 inch wire, with a mesh of 88×88 wires, providing openings of substantially 0.0079 inch square, with an open area of 47.9 percent; and a fourth filter member positioned downstream of the third filter member and being formed of a square weave of 0.0011 inch wire, with a mesh of 325×325 wires, providing openings of substantially 0.0020 inch square, with an open area of 41.6 percent.

25. The sodding tube assembly of claim 24 wherein said wires are formed of stainless steel.

26. The sodding tube assembly of claim 16 wherein said plurality of filter members are coated with a material selected to reduce the surface energy of said wires.

27. The sodding tube assembly of claim 26 wherein said plurality of filter members are coated with parylene.

28. The sodding tube assembly of claim 16 wherein said tubular body of said inlet fitting and filter pack assembly defines a stepped through bore; said tubular body including a cylindrical portion receivable into one of said pair of opposite ends of said tubular member; a sealing member disposed in sealing relation with said tubular body and said elongate tubular member, and a nut member engaging said inlet fitting and filter pack assembly and sealingly securing said tubular body thereto.

29. The sodding tube assembly of claim 28 wherein said stepped through bore of said inlet fitting and filter pack assembly further receives a plurality of spacer members interposed individually between adjacent ones of said plurality of filter members.

30. The sodding tube assembly of claim 28 wherein said tubular body further includes a closure member closing an end of said stepped through bore remote from said tubular member, said closure member defining a recess confronting a first of said plurality of filter members and defining a first one of said plurality of turbulent-flow chambers.

31. The sodding tube assembly of claim 16 further including a conduit for connecting a source of the isolated cells from tissues with said sodding tube assembly, said conduit at each end thereof including a male luer-type connector with a freely rotational fastening collar, and said sodding tube assembly including a female luer-type connector carried upon said inlet fitting and filter pack assembly and communicating with said inlet flow path for receiving the quantity of cells in liquid and communicating the cells and liquid together into the lumen of the graft.

32. A method of sodding cells onto the inner lumenal surface of an elongate tubular vascular graft having a porous wall, said method comprising the steps of:

provniding an elongate tubular shape-retaining body defining a flow path extending there along and an elongate sodding chamber therewithin;

disposing the graft within and along said sodding chamber;

plugging a distal end of the graft;

providing a pellet of aggregated cells;

flushing said pellet of aggregated cells into said elongate tubular body with a flow of liquid;

subjecting said cell aggregations to a series of successively finer filtrations to prevent aggregations of cells above a determined size from reaching said graft and sodding chamber;

introducing the liquid and individual cells along with aggregations of cells below said determined size into the lumen of the tubular vascular graft;

flowing said fluid through the porous wall of the graft while sodding the individual cells and aggregations below said determined size onto the inner lumenal surface of the graft; and preventing reflux of liquid along said flow path from an outlet toward said sodding chamber.

* * * * *